United States Patent [19]

Rajadhyaksha et al.

[11] 4,016,223
[45] Apr. 5, 1977

[54] PROSTAGLANDIN DEHYDROGENASE INHIBITING AGENTS

[75] Inventors: Vithal J. Rajadhyaksha, Mission Viejo, Calif.; Richard A. Schroer, West Nyack, N.Y.; Phillip J. Brock, Mountain View; Earl R. Krueger, Anaheim, both of Calif.

[73] Assignee: Nelson Research & Development Company, Irvine, Calif.

[22] Filed: Aug. 7, 1975

[21] Appl. No.: 602,735

[52] U.S. Cl. .................. 260/946; 260/940; 260/944; 260/923; 424/210; 424/211; 424/214

[51] Int. Cl.² ............ C07F 9/09; A01N 9/36

[58] Field of Search .............. 260/946, 944

[56] References Cited
UNITED STATES PATENTS 3,851,019  11/1974  Hogberg et al. .................. 260/946

Primary Examiner—Anton H. Sutto
Attorney, Agent, or Firm—Martin A. Voet

[57] ABSTRACT

Novel prostaglandin dehydrogenase inhibiting agents having the structural formula

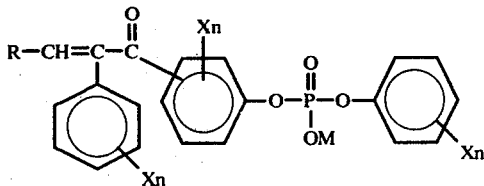

wherein R is H or 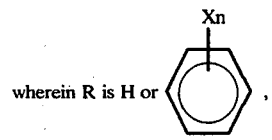 , M is H or a pharmaceutically acceptable salt, X is hydrogen, dialkylaminomethyl, lower alkyl, lower alkoxy, aryl, substituted aryl, halogen, cyano, nitro, trihaloalkyl, $-NR_1R_2$ or $-NHCOR_1$ where $R_1$ and $R_2$ are hydrogen, lower alkyl or $NH_2$ and $n$ is 0–5.

2 Claims, No Drawings

PROSTAGLANDIN DEHYDROGENASE INHIBITING AGENTS

BACKGROUND OF THE INVENTION

1. Field of the Invention

This invention relates to novel compounds. More particularly, the present invention relates to compounds having prostaglandin dehydrogenase blocking activity.

2. Background of the Prior Art

Prostaglandins are local hormones related to fatty acids occurring naturally in the body which act mainly as intercellular and/or intraorgan regulators. Enzymes also exist naturally in the body which synthesize or inactivate the prostaglandins. The enzyme which synthesizes the prostaglandins is known as prostaglandin synthetase. The enzyme which inactivates the prostaglandins is known as prostaglandin dehydrogenase. Many therapeutically useful compounds are known to act through the mechanism of blocking prostaglandin synthesis by interfering or blocking the prostaglandin synthetase e.g. indomethacin and aspirin. It would be desirable to identify a compound or family of compounds having prostaglandin dehydrogenase blocking activity in that desirable prostaglandin-induced activity could be sustained for longer periods of time by blocking or inhibiting the inactivating action of the prostaglandin dehydrogenase enzyme.

SUMMARY OF THE INVENTION

We have now unexpectedly discovered a family of novel compounds which are useful in selectively blocking or inhibiting the activity of the enzyme prostaglandin dehydrogenase.

This invention therefore relates to novel compounds having the structural formula

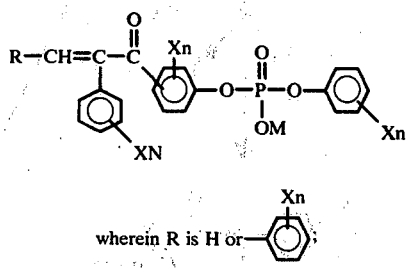

M is H or a pharmaceutically acceptable salt; X is selected from the group consisting of hydrogen, lower alkyl, lower alkoxy, aryl, substituted aryl, halogen, cyano, nitro, trihaloalkyl, $-NR_1R_2$ and $-NHCOR_1$, where $R_1$ and $R_2$ are selected from the group consisting of hydrogen, lower alkyl and $NH_2$; and $n$ is 0–5. The position of the carbonyl group $$\left( -\overset{O}{\underset{\|}{C}}- \right)$$

with respect to the phenyl phosphate ester can be either 2, 3 or 4 but preferably at the 4-position.

DETAILED DESCRIPTION OF THE INVENTION

The active compound of the present invention has the following structural formula

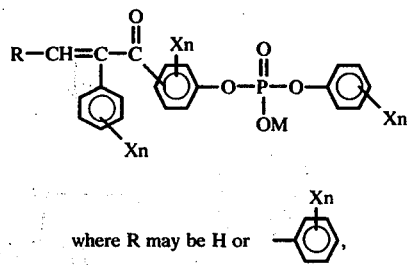

where M is H or a pharmaceutically acceptable salt, e.g., a metal salt such as, for example, sodium or potassium. X may be hydrogen, lower alkyl or lower alkoxy, that is, straight or branch chain alkyl groups having 1–8 and preferably 1–4 carbon atoms, halogen, such as, for example, F, Cl, or Br; cyano, nitro, trihaloalkyl such as $CF_3$, aryl, such as phenyl and substituted aryl, $-NR_1R_2$ and $-NHCOR_1$, where $R_1$ and $R_2$ are hydrogen, lower alkyl or $NH_2$, and $n$ is 0 to 5. The position of the carbonyl group with respect to the phenyl phosphate ester group can be either 2, 3 or 4 but preferably at the 4-position. The configuration about the carbon-carbon double bond can be Z or E.

A preferred embodiment of this invention relates to the phenyl phosphate ester of 1-(4-hydroxyphenyl)-2,3-diaryl-2-propen-1-one having the following structural formula

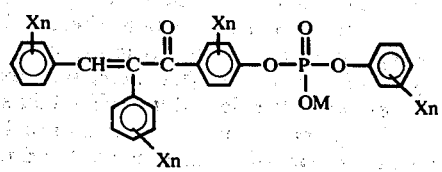

where M is H or a pharmaceutically acceptable salt, e.g., a metal salt; X is H, halogen, $NO_2$, $CF_3$, lower alkyl, CN or amino and $n$ is 0–5.

The foregoing class of compounds exhibits particularly good activity against 15—OH prostaglandin dehydrogenase and represents a preferred subgroup of compound within the scope of this invention.

The nuclear hydroxy substituted 1,2,3-triaryl-2-propen-1-one of this invention wherein R is aryl or substituted aryl are conveniently prepared by reacting an equimolar amount of a nuclear hydroxy substituted 1,2-diarylethanone with an equimolar amount of appropriately substituted aryl aldehyde in presence of piperidine at 30°–60°. The condensation product thus obtained is then hydrolyzed by refluxing with glacial acetic acid. This is outlined in the scheme below:

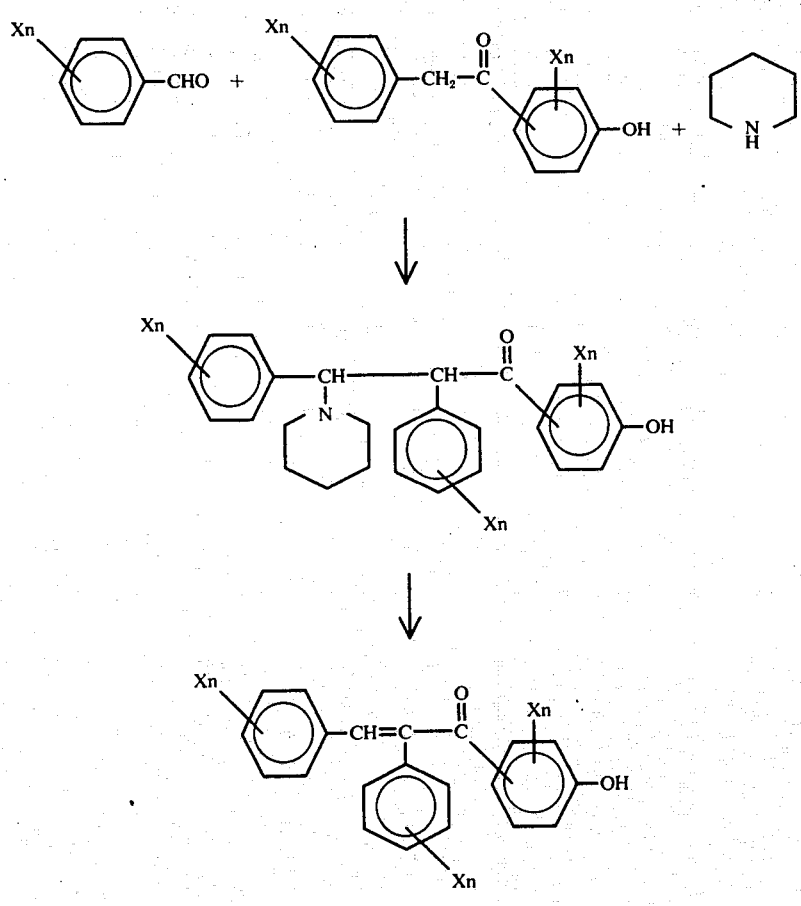

wherein X and n have the same meaning as before.

The compounds of the invention where R is H are conveniently prepared by the reaction of a nuclear hydroxy substituted 1,2-diarylethanone with formaldehyde or paraformaldehyde and the acid addition salt of a di-lower alkylamine, piperidine or morpholine and the Mannich amine salt is then converted directly to the nuclear hydroxy substituted 1,2-diphenyl-2-propen-1-one by decomposition, as for example, by heating the Mannich salt at temperatures above room temperature and, preferably, in the presence of a solvent of high dielectric constant such as dimethylformamide or, alternatively, the salt of the Mannich amine is treated with a weak base, such as sodium bicarbonate, to obtain the corresponding free Mannich amine derivative, which is then decomposed to the desired nuclear hydroxy substituted 1,2-diaryl-2-propen-1-one. The following illustrates this method of preparation:

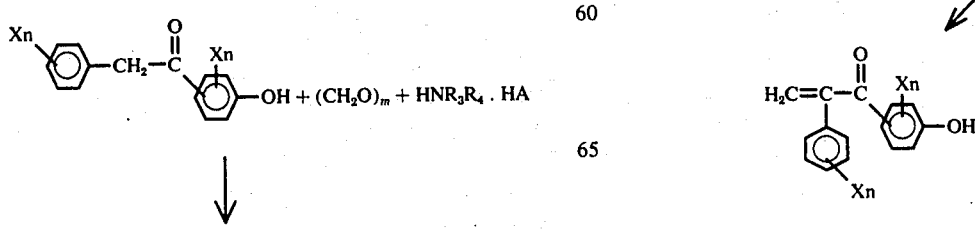

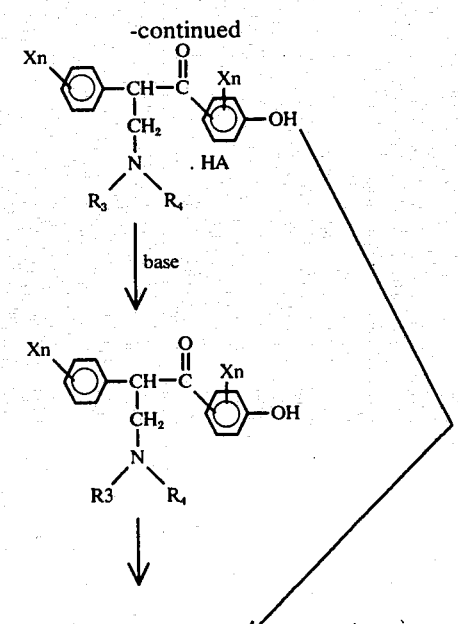

wherein X and n are as defined above, $HNR_3R_4$ is a secondary amine, for example, an amine selected from the group consisting of dilower alkylamine, piperidine and morpholine; HA is the moiety derived from an organic or inorganic acid capable of forming salts with amines, for example, hydrochloric acid, etc., and m is a positive integer of 1 or greater.

An alternate method for preparing the nuclear hydroxy substituted 1,2-diphenyl-2-propen-1-one also comprises treating a nuclear hydroxy substituted 1,2-diarylethanone with formaldehyde or paraformaldehyde and the salt of a secondary amine to obtain the Mannich salt as in the foregoing method. The Mannich salt is then converted to the free Mannich amine which is then treated with a suitable quaternizing agent to obtain the corresponding quaternary ammonium salt and then converting the said quaternary ammonium derivative to the desired nuclear hydroxy 1,2-diaryl-2-propen-1-one by treatment with a base, for example, with an aqueous solution of sodium bicarbonate. The following equation illustrates this method of preparation:

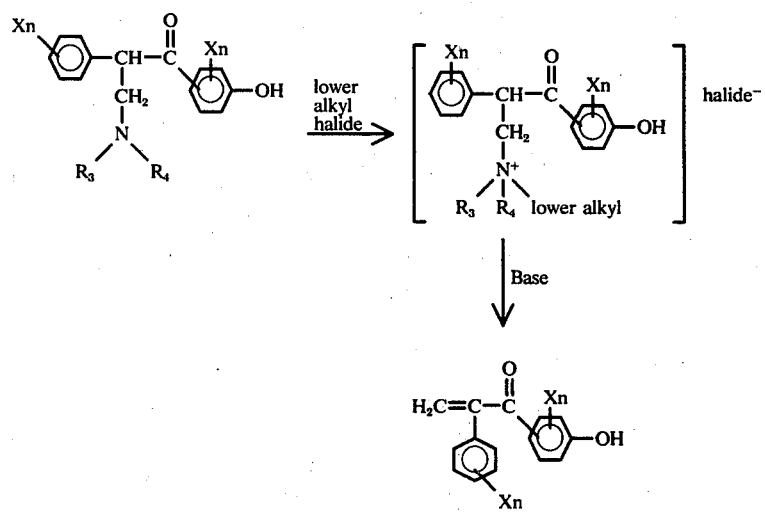

wherein $R_3$, $R_4$, X and n are as defined before.

Another method for preparing nuclear hydroxy substituted 1,2,3-triaryl-2-propen-1-one comprises treating a suitable nuclear hydroxy substituted 1,2,3-triaryl-1-propanone with a halogenating agent, for example, with chlorine, bromine, iodine monochloride, etc., followed by the reaction of the halogenated derivative with a dehydrohalogenating agent. Dehydrohalogenating reagents which are suitable in the process, include, for example, tertiary amines, metal halides, alkali metal acetates, alkali metal carbonates, etc. Specifically, triethylamine, anhydrous lithium chloride, lithium bromide, silver acetate, potassium acetate, silver fluoride and potassium carbonate have been found to be particularly effective in the dehydrohalogenation reaction.

In general, the dehydrohalogenation reaction may be carried out in an inert solvent in which all the reactants are reasonably soluble, for example, in dimethylformamide, especially when lithium chloride or lithium bromide is the dehydrohalogenating agent employed. The process is illustrated by the following:

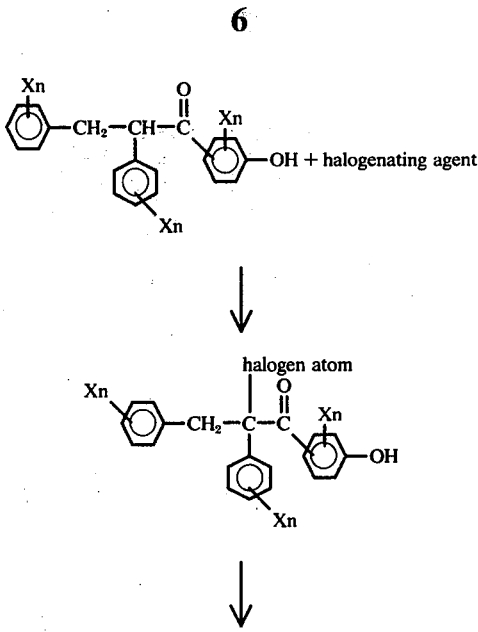

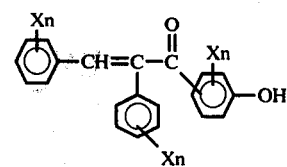

wherein X and n have the same meaning as before.

Another approach to the synthesis of nuclear hydroxy substituted 1,2,3-triaryl-2-propen-1-one is by reacting carbonyl compounds, in the presence of proton acceptors containing metal, with such derivatives of carbonyl compounds as contain a (>C=N—) group in place of a (>C=O) group and moreover contain a (—CH$_2$—) group vicinal to the imino carbon atom and then dehydrating and hydrolyzing the reaction product.

The process is described below:

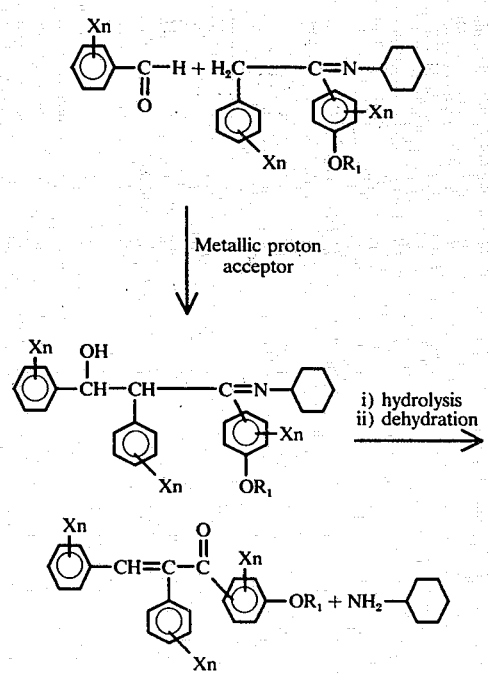

where X, $R_1$ and $n$ have the same meaning as before.

Suitable derivatives of carbonyl compounds in which the C=O group is replaced by a C=N— group and which contain a methylene group vicinal to the iminocarbon atom are the reaction products of nuclear hydroxy or alkoxy substituted 1,2-diarylethanones with aliphatic, cycloaliphatic, araliphatic and aromatic amines, hydrazines or the oxygen derivatives of hydroxylamine.

Suitable metal containing proton acceptors are organic compounds such as lithium methyl, lithium butyl, lithium phenyl, sodium phenyl, alkali acetylene compounds and Grignard compounds. Compounds of the alkali metals with organic amines and ammonia are particularly suitable. Examples of such compounds are lithium amide, sodamide, potassium amide, lithium diisopropylamide, lithium diethylamide, etc.

Preferred solvents for the foregoing reaction are ethers, such as diethylether, tetrahydrofuran, dioxane, hydrocarbons, such as hexane, octane, cyclohexane, benzene and toluene and dimethylformamide, n-methylpyrrolidone and dimethylsulfoxide. The reaction is suitably carried out in an inert atmosphere in the range between room temperature and −70° C.

The starting material for all above reactions, the nuclear hydroxy substituted 1,2-diaryl-ethanones can be conveniently prepared by Friedel-Crafts method by reacting approximately substituted aryl acetyl chloride with excess alkoxybenzene in presence of a catalyst, for example, anhydrous aluminium chloride, followed by demethylation of the alkyl ether. Pyridine-hydrochloride, anhydrous aluminium chloride or boron trihalides are preferred as dealkylating agents. Methoxy- or ethoxybenzenes are preferably used. The process is outlined below:

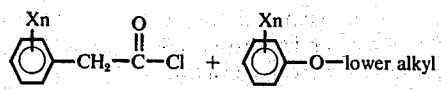

wherein X and $n$ are as indicated before.

It frequently occurs that the foregoing Friedel-Crafts reaction produces a mixture of the 2- and 4-isomers of the ethers, as for example, when the phenol ether employed has a 3-chloro or 3-methyl substituent. In such an instance, they are separated by fractional distillation of the nuclear hydroxy derivatives obtained after dealkylation and may then be etherified if necessary by conventional means to the corresponding pure ether compounds.

The nuclear hydroxy substituted 1,2,3triaryl-1-propanone, used as starting materials, are conveniently prepared by alkylation of a nuclear alkoxy substituted 1,2-diarylethanone obtained before in presence of a base. Suitable alkylating agents are aralkyl halides, such as α-chlorotoluene, α,4-dibromotoluene, etc. Preferred base is potassium tertiary butoxide and preferred solvent is dimethylsulfoxide. Cleavage of the ether linkage gives the desired 1-propanone derivative as outlined in the following:

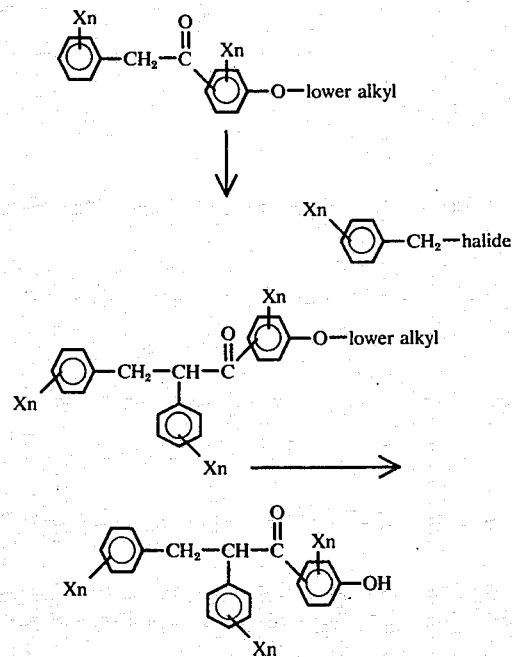

wherein X and $n$ have the same meaning as before.

Phosphorylation of the nuclear hydroxy substituted 1,2,3-triaryl-2propen-1-one can be carried out by treatment with conventional phosphorylating agents as described in Houben-Weyl's "Methoden der Organischen Chemie" Band XII, Teil 2, p. 226, and the heading "Phosphorylation" by D. M. Brown, p. 75, in "Advances in Organic Chemistry" Vol. 3, Interscience Publishers, 1963, and E. Cherbuliez in "Organic Phosphorous Compounds," Vol. 6, Ed. by G. M. Kosolapoff and L. Maier, Wiley-Interscience, 1973, p. 211.

The preferred method comprises in treating the nuclear hydroxy substituted 1,2,3-triaryl-2propen-1-one with an aryl dichlorophosphate, for example, phenyl dichlorophosphate in presence of a tertiary base at −20° to −10° C. Preferred tertiary bases are pyridine and diisopropylethylamine. Excess phosphorylating agent is generally employed and sixfold excess is preferred. The diester monochloride is then hydrolyzed to the free phosphoric acid diester.

In another method, phenyl phosphoric acid is allowed to react in an activated form with about one mole of the nuclear hydroxy substituted 1,2,3-triaryl-2-propen-1-one. This reaction may for instance be carried out in the presence of about two moles of a tertiary amine, e.g., triethylamine, using a suitable solvent, for instance pyridine. After the condensation has been completed, water is added making it possible to isolate the diester. This procedure can be similarly applied for condensing phenol or substituted phenol with a phosphoric acid monoester of the nuclear hydroxy substituted 1,2,3-triaryl-2-propen-1-one of the following formula:

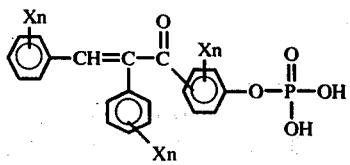

where X and n have the same meaning as before. The phosphoric acid monoesters can be prepared as described in the foregoing references.

Yet another but similar method involves the treatment of phenyl phosphoric acid and the nuclear hydroxy substituted 1,2,3-triaryl-2-propen-1-one in presence of a condensing agent such as carbonyldiimidazole.

Another method comprises the condensation of the nuclear hydroxy substituted 1,2,3-triaryl-2propen-1-one and phenol in the presence of 2-chloromethyl-4-nitrophenyl dichlorophosphate.

The examples which follow illustrate the phenyl phosphate esters of the 1-(4-hydroxyphenyl)-2,3-diphenyl-2-propen-1-ones of this invention and the method by which they are prepared. However, the examples are illustrative only and it should be apparent to one having only ordinary skill in the art that all of the products embraced by the general formula, supra, may also be prepared in an analogous manner by substituting the appropriate starting materials for those set forth in the examples. All temperatures are in degrees centigrade.

EXAMPLE 1

Method of making 1-(4-hydroxyphenyl)-2,3-diphenyl-2-propen-1-one having the structural formula

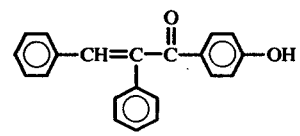

A. 9 g (0.0424 moles) 1-(4-hydroxyphenyl)-2-phenylethanone, 4.5 g (0.0424 moles) benzaldehyde, 3.38 g (0.0397 moles) piperidine and 18 ml methanol were combined and let stir for about 3 hours at room temperature. By this time the mixture had solidified. After keeping overnight, the solid was filtered and washed with a small amount of methanol. After drying 11.5 g (70%) of a grey powder with m.p. 144°–147° was obtained.

B. 10 g (0.0259 moles) of this material was combined with 110 ml glacial acetic acid and the mixture refluxed for 4½ hours. After cooling, this was diluted to 650 ml with water whereupon a brown powder precipitated. This was filtered off and dried. One recrystallization from methanol/water gave 4.2 g (54%) of a light brown powder. M.P. 186°–190°.

IR (Nujol):
3440, 1638, 1600, 1580, 1508, 1321, 1307, 1282, 1267, 1233, 1187, 1170, 1109, 1086, 1065, 1028, 930, 920, 878, 852, 838, 774, 767, 718, 692 cms$^{-1}$.

NMR (Acetone-D$_6$ + TMS)
7.9 δ (doublet); 7.24 δ (singlet); 7.2 δ (singlet); 6.8 – 7.2 δ (multiplet).

EXAMPLE 2

Method of making 1-(4-hydroxyphenyl)-3-(4-chlorophenyl)-2-phenyl-2-propen-1-one having the structural formula

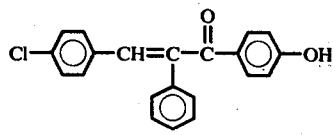

9.4 g (0.0443 mole) of 1-(4-hydroxyphenyl)-2-phenylethanone, 6.23 g (0.0443 mole) of 4-chlorobenzaldehyde and 3.53 g (0.0415 mole) of piperidine in 19.3 ml of methanol was stirred at 35° and then kept overnight. It was worked up as under Example IA to give 14.5 g (83%) of crude product. 14 g (0.0333 mole) of the crude phenol was mixed with 140 ml of glacial acetic acid and refluxed for 4 hours. Work up as under Example IB followed by recrystallization from methanol gave 3.7 g (34%) of pure product, m.p. 179°–181°.

NMR (D$_6$-Acetone + TMS)
8.2 – 8.4 (doublet); 7.1 – 7.7 (multiplet);
IR ((Nujol):
3460, 1638, 1602, 1581, 1510, 1488, 1405, 1310, 1280, 1263, 1236, 1170, 1109, 1092, 1067, 1013, 952, 920, 910, 880, 852, 823, 769, 730, 717, 710 and 699 cms$^{-1}$.

EXAMPLE 3

Method of making 1-(4-hydroxyphenyl)-3-(4-bromophenyl)-2-phenyl-2-propen-1-one having the structural formula

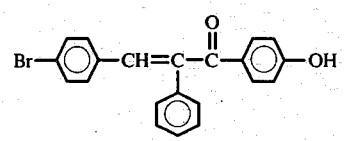

8.02 g (0.0378 mole) of 1-(4-hydroxyphenyl)-2-phenylethanone, 7.0 g (0.0378 mole) of 4-bromobenzaldehyde, 3.01 g (0.0353 mole) of piperidine and 16.5 ml of methanol was treated or mentioned under Example IA to give 13 g (74%) of crude product. 12.5 g (0.027 mole) of this phenol was refluxed with 120 ml and worked up as in Example IB. Recrystallization from methanol gave 5.2 g (51%) of the product.
IR (Nujol):
3460, 1637, 1601, 1581, 1510, 1485, 1400, 1310, 1280, 1262, 1233, 1169, 1108, 1073, 1065, 1010, 920, 910, 880, 853, 820, 768, 728 cms$^{-1}$.
NMR (D$_6$-Acetone + TMS)
8.1 – 8.3 δ (doublet); 7.25 – 7.9 δ (multiplet);

EXAMPLE 4

Method of making 1-(4-hydroxyphenyl)-2-(4-chlorophenyl)-3-phenyl-2-propen-1-one having the structural formula

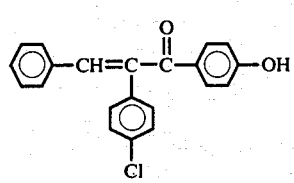

8 g (0.0324 mole) of 1-(4-hydroxyphenyl)-2-(4-chlorophenyl)ethanone (prepared by Friedel-Craft reaction between methoxybenzene and 4-chlorophenylacetylchloride, followed by demethylation of the methyl ether with pyridine hydrochloride) was treated with 3.44 g (0.0324 mole) of benzaldehyde and 2.58 g (0.304 mole) of piperidine in 15 ml of methanol at 60° C and worked up as under Example IA gave 9.0 g of crude product. 8.5 g of this material on refluxing with 85 ml of glacial acetic acid for 4 hours and was worked up as under Example IB. Trituration with hot methanol and cooling gave 3 g (44.5%) of crystalline material, m.p. 228°.
IR (Nujol):
3465, 1632, 1600, 1578, 1508, 1278, 1263, 1225, 1170, 1088, 1013, 883, 845, 793, 770, 740, and 720 cms$^{-1}$.
NMR (D$_6$-Acetone + TMS)
8.1 – 8.3 δ (doublet); 7.1 – 7.3 δ (doublet); 7.4 – 7.6 δ (multiplet).

EXAMPLE 5

Method of making 1-(4-hydroxyphenyl)-2-(4-bromophenyl)-3-phenyl-2-propen-1-one, having the structural formula

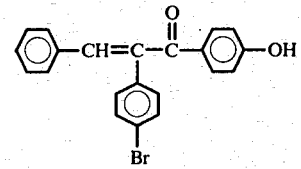

10 g (0.0343 mole) of 1-(4-hydroxyphenyl)-2-(4-bromophenyl)ethanone (prepared from 4-bromophenylacetylchloride and methoxybenzene followed by demethylation with pyridine hydrochloride), 3.65 g (0.0343 mole) of benzaldehyde, 2.75 g (0.0325 mole) of piperidine in 15 ml of methanol at 50° gave 4.9 g (31%) of yellowish white solid. Evaporation of the mother liquor gave 10 g of foamy material which showed three spots on TLC. The major spot was identical with the pure product.
4.8 g (0.0103 mole) of this material was refluxed with 100 ml of acetic acid for 4 hours. Work up as in the previous examples, followed by recrystallization from warm methanol gave 1.1 g (28%) of the desired product.
10 g of the foamy material gave additional 1.8 g (22%) of pure phenol derivative on hydrolysis.
IR (Nujol):
3344, 1637, 1608, 1575, 1513, 1488, 1361, 1314, 1280, 1264, 1227, 1167, 1081, 1070, 1058, 1009, 939, 913, 881, 851, 833, 813, 793, 764, 740, 719, 709, 699 and 687 cms$^{-1}$.
NMR (D$_6$-Acetone + TMS)
8.1 – 8.3 δ (doublet); 7.1 – 7.3 δ (doublet); 7.4 – 7.9 δ (multiplet).

EXAMPLE 6

Method of making 1-(4-hydroxyphenyl)-2,3-di(4-chlorophenyl)-2-propen-1-one, having the structural formula

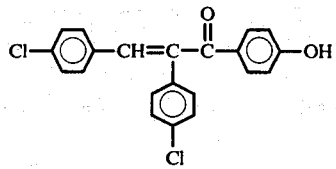

8 g (0.0324 mole) of 1-(4-hydroxyphenyl)-2-(4-chlorophenyl)ethanone, 4.56 g (0.0324 mole) of 4-chlorobenzaldehyde, 2.58 g (0.0302 mole) of piperidine in 14.2 ml of methanol was stirred at 60° overnight and worked up as in previous examples to give 10.5 g (71%) of crude product.
10 g (0.022 mole) of this crude material was refluxed with 100 ml of acetic acid for 4 hours and worked up as before. Yield 5.5 g (68%), m.p. 132°–136°.
I.R. (Nujol):
3467, 1633, 1601, 1579, 1510, 1488, 1310, 1278, 1263, 1230, 1171, 1088, 1067, 1013, 887, 860, 845, 825, 798 and 765 cms$^{-1}$.
NMR (D$_6$-DMSO + TMS); 8.1 – 8.3 δ (doublet); 7.1 – 7.3 δ (doublet); 7.4 – 7.8 δ (multiplet).

EXAMPLE 7

Method of making 1-(4-hydroxyphenyl)-3-(4-nitrophenyl)-2-phenyl-2-propen-1-one, having the structural formula

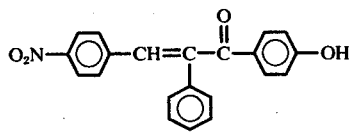

5 g (0.0235 mole) of 1-(4-hydroxyphenyl)-2-phenylethanone, 3.56 g (0.0235 mole) of 4-nitrobenzaldehyde and 1.88 g (0.0221 mole) of piperidine in 10 ml of methanol on stirring overnight at room temperature gave a yellow solid, m.p. 153°–157°. This solid was taken in 100 ml of glacial acetic acid and refluxed for 4½ hours. The resultant clear yellow solution was poured into 700 ml of cold water. The resulting oil was extracted into chloroform, chloroform solution washed with water, dried and concentrated. An orange oil was obtained which slowly crystallized. This material upon purification through column chromatography and recrystallization afforded pure product. M.P. 173°–177°.
NMR ($D_6$-Acetone);
 8.1 – 8.4 δ (multiplet); 7.7 δ (singlet); 7.55 δ (singlet); 7.05 – 7.4 δ (triplet).
IR (Nujol):
 3360, 1640, 1608, 1580, 1520, 1495, 1420, 1358, 1318, 1292, 1280, 1225, 1175, 1120, 1082, 1074, 905, 900, 860, 780, 770, 760, 730, 720, 710, 680, 620, 605 $cms^{-1}$.

EXAMPLE 8

Method of making 1-(4-hydroxyphenyl)-3-(4-aminophenyl)-2-phenyl-2-propen-1-one having the structural formula

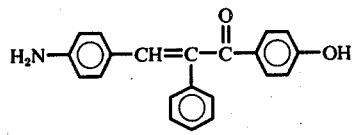

540 mg (0.00146 mole) of the material obtained under Example 7 was taken in 1 ml of ethanol and 1.5 ml of 37% hydrochloric acid. A solution of 1.13 g (0.005 mole) of stannous chloride in 4 ml of ethanol was added dropwise. The stirred mixture was refluxed for 1 hour and the solution was concentrated to a dark red oil. The oil was washed with saturated sodium bicarbonate solution and was extracted with chloroform. Chloroform solution was washed with water, dried and concentrated to give 430 mg of orange red material. This material was homogeneous on TLC.
IR (Nujol):
 3370, 1635, 1580, 1545, 1515, 1310, 1280, 1235, 1190, 1165, 910, 830, 760, 700 $cms^{-1}$.
NMR ($CDCl_3$);
 δ 7.9 – 8.2 doublet; δ 6.4 – 7.7 multiplet; δ 4.5 – 5.5 broad singlet;

EXAMPLE 9

Method of making 1-(4-hydroxyphenyl)-2-phenyl-2-propen-1-one, having the structural formula

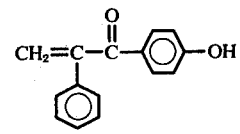

15 g (0.0707 mole) of 1-(4-hydroxyphenyl)-2-phenylethanone, 2.8 g (0.897 mole) of paraformaldehyde, 7.7 g (0.0912 mole) of dimethylamine hydrochloride, 15 ml of ethanol and 0.3 ml of concentrated hydrochloric acid were combined, refluxed and filtered on cooling. 2 g of this solid was mixed with 100 ml of saturated sodium bicarbonate solution and the suspension was heated for 3 hours at 80°. After cooling the mixture was acidified, extracted with ether and concentrated to an oil which solidified. This material was passed through a silica gel column to obtain 70% pure product, the contaminant being the starting ethanone derivative. The crude product was obtained in 13% yield after several recrystallizations.
IR (Nujol):
 3344, 1675, 1642, 1608, 1575, 1515, 1494, 1340, 1332, 1282, 1217, 1163, 1109, 1074, 1024, 988, 966, 952, 855, 840, 800, 794, 775, 727, and 704 $cms^{-1}$.
NMR ($CDCl_3$ + TMS)
 δ 8.0 – 8.25 multiplet; δ 7.4 – 7.65 multiplet; δ 6.9 – 7.25 multiplet; δ 6.25 singlet; δ 5.7 singlet.

EXAMPLE 10

Method of making 1-(4-hydroxyphenyl)-2,3-diphenyl-2-propen-1-one phenyl hydrogen phosphate monosodium salt having the structural formula

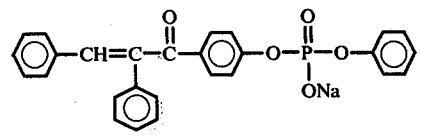

4 g (0.0133 moles) of 1-(4-hydroxyphenyl)-2,3-diphenyl-2-propen-1-one obtained in Example 1 was dissolved in 60 ml of dry pyridine and this solution was added dropwise over a period of 2 hours to a stirred mixture of 17 g (0.0806 moles) phenyl dichlorophosphate and 2 ml pyridine maintained at −20° to −10°. The mixture was stirred at −20° to −10° for an additional ½ hour and then let slowly warm to room temperature overnight. 2 ml of water was slowly added to the cooled reaction mixture under stirring. Most of the pyridine was removed at 50° under reduced pressure. The residue was taken up in chloroform and this organic solution washed with 1N HCl (1 × 105 ml), 5 N HCl (3 × 100 ml) and water (2 × 150 ml). The chloroform phase was separated, dried ($MgSO_4$) and concentrated to a viscous brown oil. The oil was dissolved in methanol and neutralized to pH 7 with methanolic NaOH. This solution was concentrated and the residue washed with ether to give a light brown powder. Yield: 5.38 g (85%).

IR (Sodium salt; Nujol)
1645, 1595, 1490, 1250, 1210, 1160, 1098, 900 cms⁻¹.
NMR (free acid; CDCl₃);
Doublet at δ 7.7; Multiplet from δ 7.0 – 7.5;

EXAMPLE 11

Method of making 1-(4-hydroxyphenyl)-3-(4-chlorophenyl)-2-phenyl-2-propen-1-one phenyl hydrogen phosphate monosodium salt having the structural formula

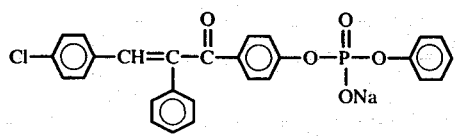

A solution of 1.5 g (0.00448 mole) of the phenol (obtained under Example 2) in 20 ml of dry pyridine was added dropwise with stirring to a mixture of 5.69 g (0.0269 mole) of phenyl dichlorophosphate at −20° C. Following the procedure, as outlined under Example 10, 2 g (67.12%) of the pure sodium salt of the phosphate diester was obtained.

IR (free acid; neat);
3070, 1655, 1598, 1490, 1458, 1443, 1412, 1385, 1313, 1260, 1200, 1167, 1093, 1070, 1027, 1015, 1005, 960, 883, 852, 827, 770, 729, 705, and 693 cms⁻¹ of the free acid.

NMR (CDCl₃ + TMS);
δ 9.5 (broad singlet); δ 8.0 – 8.2 (doublet); δ 7.25 – 7.65 (multiplet).

EXAMPLE 12

Method of making 1-(4-hydroxyphenyl)-3-(4-bromophenyl)-2-phenyl-2-propen-1-one phenyl hydrogen phosphate monosodium salt, having the structural formula

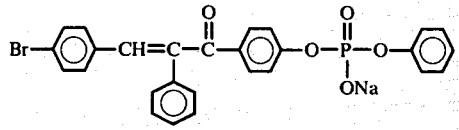

Following the reaction procedure in Example 10, from 2.056 g (0.00542 mole) of the phenol (obtained under Example 3) and 6.32 g (0.03 mole) of phenyl dichlorophosphate was obtained 2.7 g (89.37%) of the pure monosodium salt of the phosphate diester.

IR (Free acid; neat);
3060, 2920, 1650, 1598, 1488, 1440, 1410, 1380, 1310, 1280, 1255, 1200, 1163, 1102, 1071, 1025, 1010, 960, 881, 852, 822, 768, 723, 702 and 690 cms⁻¹.

NMR (Free acid; CDCl₃ + TMS)
δ 11.0 (broad singlet); δ 8.0 – 8.25 (doublet); δ 7.1 – 7.25 (multiplet).

EXAMPLE 13

Method of making 1-(4-hydroxyphenyl)-2-(4-chlorophenyl)-3-phenyl-2-propen-1-one phenyl hydrogen phosphate monosodium salt, having the structural formula

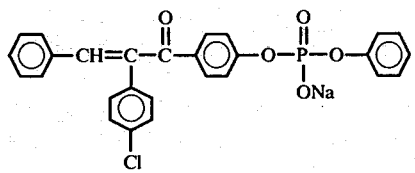

Following the procedure under Example 10, from 2 g (.00599 mole) of the phenol (obtained under Example 4) and 8 g (.04194 mole) of phenyl dichlorophosphate was obtained 2.441 g (79.5%) of the pure sodium salt of phosphate diester.

IR (Nujol) Sodium salt
3448, 1667, 1605, 1500, 1490, 1264, 1250, 1235, 1206, 1166, 1099, 1058, 1021, 1011, 913, 881, 840, 806, 766, 757 and 690 cms⁻¹.

NMR (Free acid; CDCl₃ + TMS)
δ 10.5 (broad singlet); δ 7.9 – 8.1 (doublet); δ 7.25 – 7.6 (multiplet).

EXAMPLE 14

Method of making 1-(4-hydroxyphenyl)-2-(4-bromophenyl)-3-phenyl-2-propen-1-one phenyl hydrogen phosphate monosodium salt having the structural formula

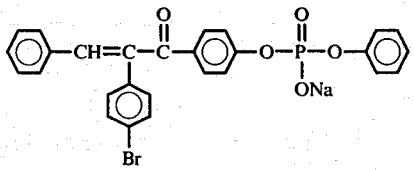

Following the procedure under Example 10, from 2.0 g (0.00527 mole) of the phenol (obtained under Example 5) and 6.68 g (0.0316 mole) of phenyl dichlorophosphate was obtained 2.64 g (89.83%) of the pure sodium salt of the phosphate diester.

IR (Nujol) — Sodium salt
3448, 1675, 1613, 1513, 1495, 1418, 1269, 1253, 1239, 1215, 1172, 1109, 1075, 1064, 1029, 1012, 917, 884, 847, 806, 770, 758, and 690 cms⁻¹.

NMR of the free acid (CDCl₃ + TMS)
δ 10.0 (broad singlet); δ7.2 – 8.1 (complex).

EXAMPLE 15

Method of making 1-(4-hydroxyphenyl)-2,3-di(4-chlorophenyl)-2-propen-1-one phenyl hydrogen phosphate monosodium salt having the structural formula

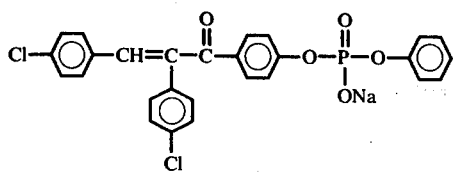

Following the procedure under Example 10, from 2 g (0.00542 mole) of the phenol (obtained under Example 6) and 6.9 g (0.0325 mole) of phenyl dichlorophosphate was obtained 2.3 g (78%) of the pure sodium salt of the diester.

IR (free acid; neat)
3067, 2930, 1655, 1595, 1492, 1411, 1312, 1258, 1200, 1166, 1092, 1015, 965, 886, 860, 827, 760, and 690 cms$^{-1}$.

NMR of the free acid (CDCl$_3$ + TMS)
δ 11.0 (broad singlet); δ 8.0 – 8.2 (doublet); δ 7.3 – 7.7 (multiplet).

EXAMPLE 16

In Vitro Prostaglandin Dehydrogenase Assay

A number of compounds were tested for their prostaglandin dehydrogenase inhibition activity.

The prostaglandin dehydrogenase enzyme was prepared from swine lung by homogenization followed by differential centrifugation to obtain the 105,000 × g supernatant. The supernatant was fractionated by ammonium sulfate with the 20–45% saturation fraction being saved. This fraction was adsorbed to Cellex-T and subsequently eluted with 0.3M KCl. The eluted fraction was concentrated and stored at −20° C as an ammonium sulfate suspension. The enzyme specific activity was approximately 100 p moles of NADH generated per minute per mg of protein.

Assay

400 –500 g of protein was incubated at 37° C with Tris HCl (pH-8.2), 50 mM KCl, 10 mM MgCl$_2$, 7 mM 2-mercaptoethanol, 250 μM NAD$^+$, 90 μM PGE$_1$ and the inhibitor under study in a total volume of 1.0 ml. All of the above components except PGE$_1$ and the inhibitor were mixed and allowed to incubate for 15 minutes at 37° C. The fluorescent emission at 460 nm (excitation at 340 nm) was measured during the last few minutes in order to establish a baseline. The PGE$_1$ (and inhibitor) was then added and the reaction monitored by following the increased fluorescence due to NADH production.

Results

The following table summarizes the results obtained with a number of subject compounds in terms of an I.D.$_{50}$.

| Compound | | I.D.$_{50}$ |
|---|---|---|
| 1 | Ph-CH=C(Ph)-C(O)-C$_6$H$_4$-O-P(O)(O$^-$Na$^+$)-O-Ph | 20 μM |
| 2 | Cl-C$_6$H$_4$-CH=C(Ph)-C(O)-C$_6$H$_4$-O-P(O)(O$^-$Na$^+$)-O-Ph | 16 μM |
| 3 | Br-C$_6$H$_4$-CH=C(Ph)-C(O)-C$_6$H$_4$-O-P(O)(O$^-$Na$^+$)-O-Ph | 19 μM |
| 4 | Cl-C$_6$H$_4$-CH=C(C$_6$H$_4$-Cl)-C(O)-C$_6$H$_4$-O-P(O)(O$^-$Na$^+$)-O-Ph | 28 μm |
| 5 | Ph-CH=C(C$_6$H$_4$-Br)-C(O)-C$_6$H$_4$-O-P(O)(O$^-$Na$^+$)-O-Ph | 35 μM |

| Compound | | I.D.$_{50}$ |
|---|---|---|
| 6 | (phenyl)–CH=C(–C(=O)–)(4-Cl-phenyl)–C(=O)–O–P(=O)(O⁻Na⁺)–O–(phenyl) | 20 μM |
| 7 | (phenyl)–CH₂–CH(phenyl)–C(=O)–(phenyl)–O–P(=O)(O⁻Na⁺)–O–(phenyl) | 100 μM |
| 8 | (phenyl)–CH=CH–C(=O)–(phenyl)–O–P(=O)(O⁻Na⁺)–O–(phenyl) | 100 μM |

The foregoing Example shows that the subject compounds (Compounds 1–6) have good to excellent prostaglandin dehydrogenase blocking activity. Though compounds 7 and 8 are structurally closely related to the compounds of this invention, they have very low prostaglandin dehydrogenase blocking activity.

We claim:

1. Compounds having the structural formula

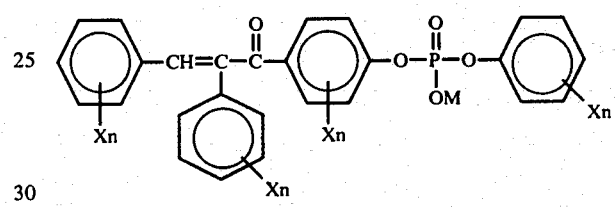

wherein M is H or a pharmaceutically acceptable salt; and X is selected from the group consisting of H, halogen, NO₂, lower alkyl and amino, and $n$ is 0–5.

2. A compound having the structural formula

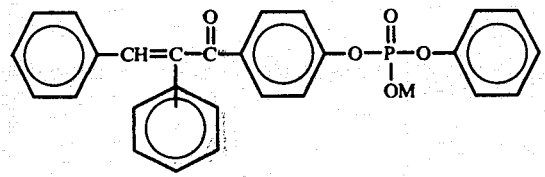

wherein M is H or a pharmaceutically acceptable salt.

* * * * *